United States Patent [19]

Alexander et al.

[11] 4,378,018

[45] Mar. 29, 1983

[54] MALE URINARY DRAINAGE DEVICE

[75] Inventors: Brian S. Alexander, Evanston; Paul O. Kay, Barrington, both of Ill.

[73] Assignee: Hollister Incorporated, Libertyville, Ill.

[21] Appl. No.: 271,082

[22] Filed: Jun. 5, 1981

[51] Int. Cl.³ .............................................. A61F 5/44
[52] U.S. Cl. ................................. 128/295; 128/760; 128/767
[58] Field of Search ................. 128/157, 79, 132, 294, 128/295, 283, 138 R, 760, 767, 144.1, 144.2, 144.3, 144.4

[56] References Cited

U.S. PATENT DOCUMENTS

| | | | |
|---|---|---|---|
| 2,604,092 | 7/1952 | Brown et al. | 128/132 R |
| 2,797,687 | 7/1957 | Crawford | 128/157 |
| 3,364,932 | 1/1968 | Beach | 128/295 |
| 3,520,305 | 7/1970 | Davis | 128/295 |
| 3,677,225 | 7/1972 | Czively | 128/294 |
| 4,187,851 | 2/1980 | Hauser | 128/295 |
| 4,284,079 | 8/1981 | Adair | 128/760 |

FOREIGN PATENT DOCUMENTS

| | | | |
|---|---|---|---|
| 18749 | 11/1980 | European Pat. Off. | 128/295 |
| 162302 | 2/1958 | Sweden | 128/157 |
| 960864 | 6/1964 | United Kingdom | 128/157 |

Primary Examiner—Richard J. Apley
Assistant Examiner—J. L. Kruter
Attorney, Agent, or Firm—Tilton, Fallon, Lungmus

[57] ABSTRACT

A male urinary drainage device composed of a thin resilient external catheter or sheath and an adhesive sealant pad for holding the sheath in place and for producing an effective seal to prevent urine backup and leakage. The pad is formed of compressible, deformable, water-resistant, and elastic sealant material and includes a ring portion adapted to seal about the penis at or directly behind the glans thereof and at least one integral strap portion projecting radially from the ring portion and intended to extend along the penile shaft. The strap portion functions primarily to provide sheath retention, whereas the ring portion coacts with the retained sheath and with the penis to serve primarily as a barrier against fluid backup.

21 Claims, 13 Drawing Figures

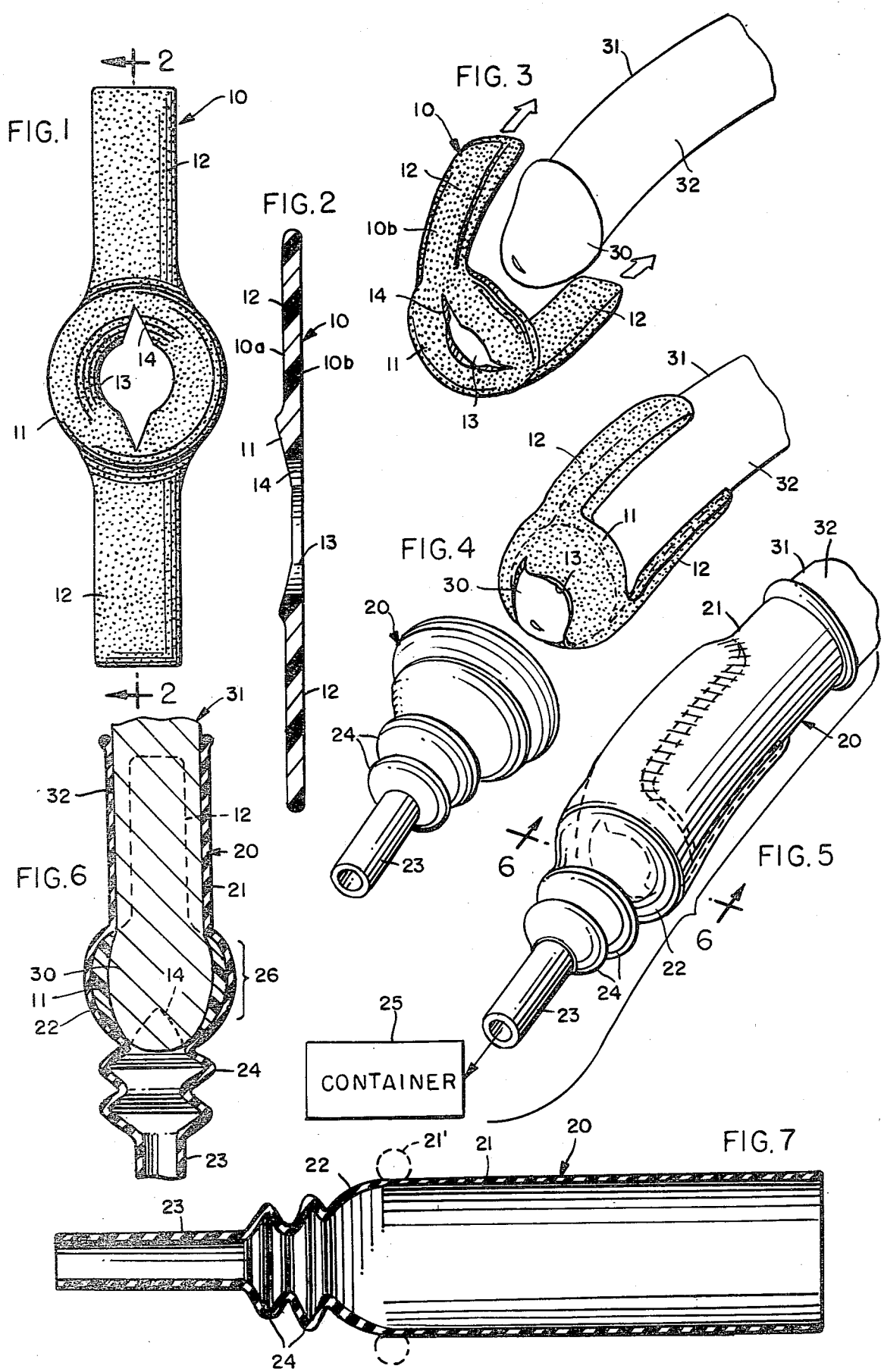

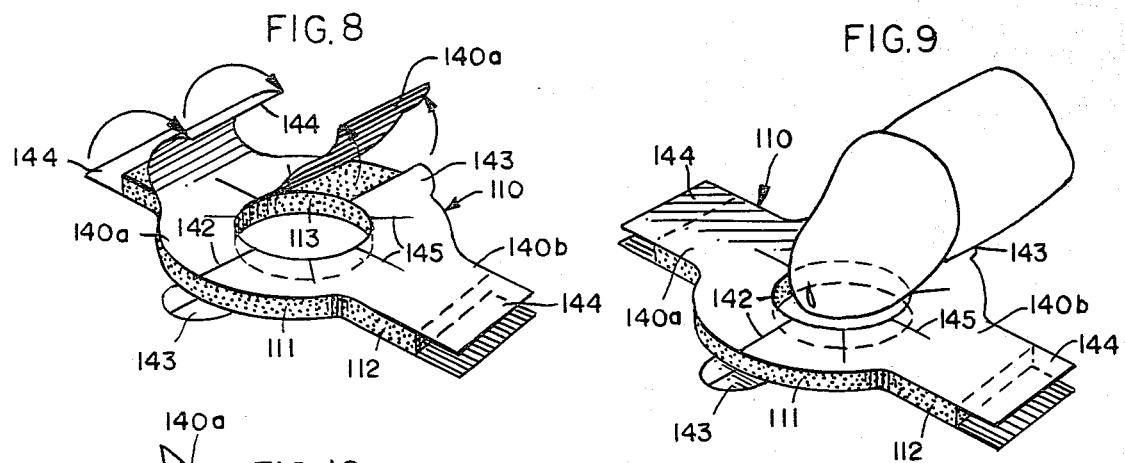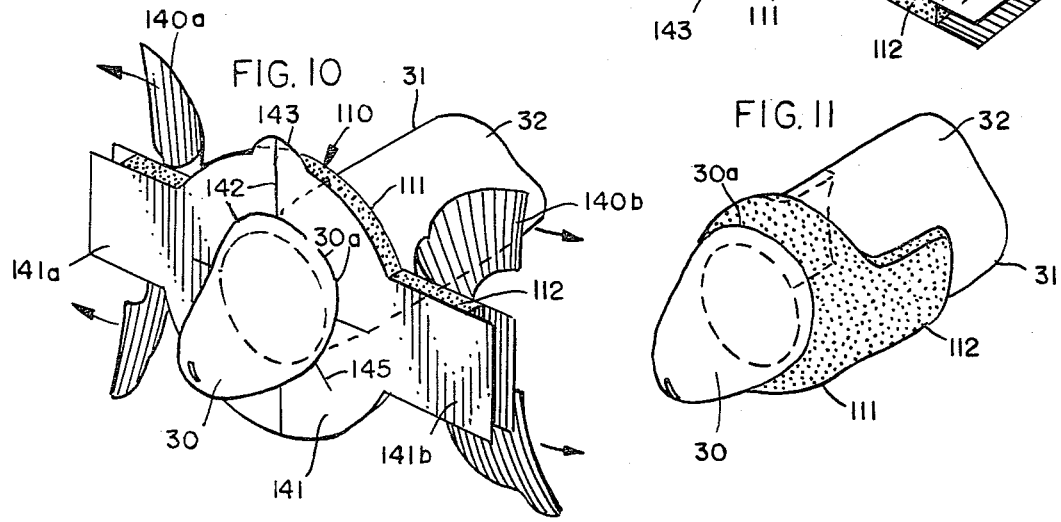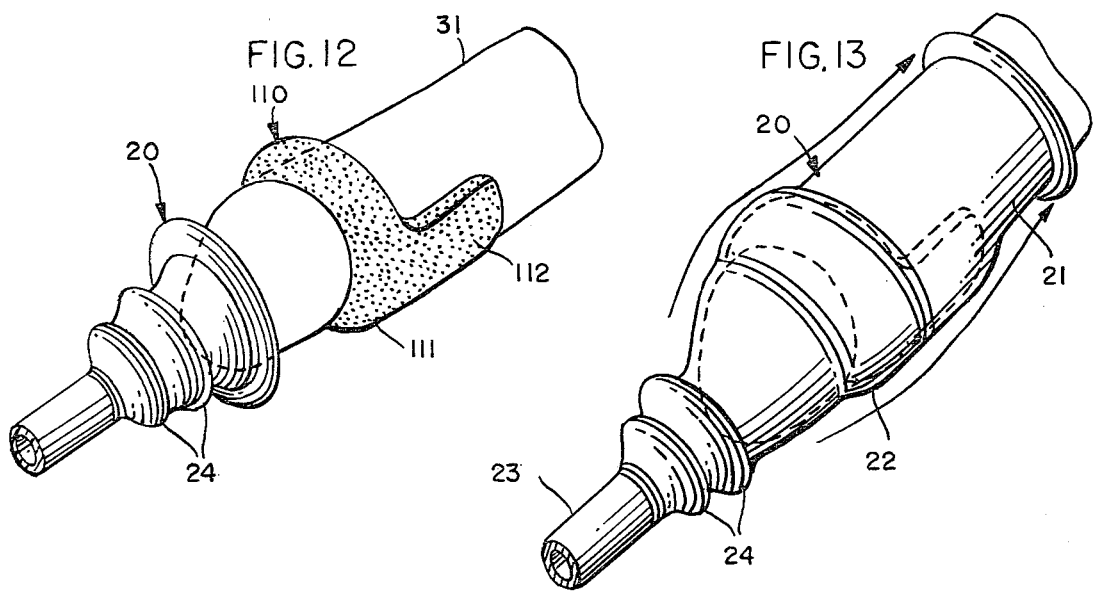

MALE URINARY DRAINAGE DEVICE

BACKGROUND

Various devices have been disclosed in the prior art for use by male patients afflicted with urinary incontinence as a result of injury, disease, advanced age, or any other cause. U.S. Pat. No. 2,940,450 discloses a drainage device in the form of a penile sheath connected to a flexible tube leading to a suitable receptacle, the sheath being held in place by drawstrings which may be tied together to produce a secure fit. In U.S. Pat. No. 3,835,857, elastic adhesive tape is wrapped about the sheath in place of drawstrings, and in U.S. Pat. No. 3,863,638 a liner is disposed beneath the sheath to reduce leakage and promote patient comfort. U.S. Pat. No. 4,187,851 discloses a method of forming such a liner in place by wrapping the penile shaft with a double-faced adhesive strip prior to application of the elastic sheath.

Those devices that have the advantage of being easily and quickly applied tend to be less effective in terms of retention and prevention of fluid backup, whereas those that are more satisfactory in the latter respects are often relatively difficult to apply and more likely to cause patient discomfort and urethral constriction. Ease of application and removal are particularly important because an incontinent patient may have other disabilities that make complicated manipulations difficult if not impossible to perform. Other patents reflecting the state of the art are U.S. Pat. Nos. 3,421,504, 3,526,227, 2,976,869, 3,339,551, 3,364,932, 3,721,243, 3,631,857, 3,788,324, 3,511,241, 3,742,953, and 2,891,546.

SUMMARY

This invention is concerned with a male urinary drainage device which overcomes the shortcomings of prior male urinary incontinence devices as described above. Specifically, it is an object of this invention to provide a male urinary incontinence device which is relatively easy to apply and remove, is retained securely in place without patient discomfort, and is highly effective in preventing liquid backup and leakage.

Briefly, the device takes the form of an elastic sheath and a resilient, deformable sealant pad. The pad has a characteristic annular portion adapted to engage the head of the penis and at least one radial strap portion designed to extend along the penile shaft. In a preferred embodiment, two such strap portions projecting from diametrically opposite sides of the annular portion are provided. The entire sealant pad is formed of a resilient, compressible, deformable, water-resistant material, and opposite sides of the pad are sufficiently tacky to provide an effective and retentive seal between the pad and penis, and between the pad and overlying sheath. More specifically, the annular portion of the pad sealingly engages both the penis and sheath to provide an effective barrier against fluid backup, whereas the strap portion performs a primary function in maintaining the sheath and pad in place. Release strips or sheets on one or both sides of the pad facilitate handling of the pad and proper placement of the pad upon a wearer.

The tubular sheath or external catheter is similar to prior sheaths except for the provision of convolutions of graduated size in the neck region between the sheath's cylindrical body portion and its reduced drainage tube portion. Such convolutions permit axial as well as radial expansion and contraction and thereby absorb tensioning forces that might otherwise occlude the lumen or reduce the effectiveness of the seal between the pad and sheath, or pad and penis, or both. When tensioning forces lateral to the drain tube portion develop, the convolutions provide for sideway expansion, thus allowing lateral displacement of the drainage tube portion without collapse or decrease in lumen cross section at the junction of the cylindrical and drainage tube portions. In addition, the convolutions increase the internal capacity of the neck region to accommodate sudden discharge of urine, thereby reducing the possibilities of fluid backup, or disengagement or damage to the drainage device, under such circumstances.

Other objects, features, and advantages of the invention will become apparent from the specification and drawings.

DRAWINGS

FIG. 1 is a plan view of the sealant pad of a drainage device embodying this invention.

FIG. 2 is a sectional view taken along line 2—2 of FIG. 1.

FIG. 3 is a perspective view illustrating a first step in fitting the sealant pad in place.

FIG. 4 depicts the pad fitted upon a wearer and a rolled sheath about to be extended over the pad.

FIG. 5 shows the device fully positioned upon a wearer.

FIG. 6 is a sectional view taken along line 6—6 of FIG. 5.

FIG. 7 is a longitudinal sectional view of the sheath component of this invention.

FIG. 8 is a perspective view of a sealant pad and release strips which constitute a second embodiment of this invention.

FIGS. 9-11 are perspective views showing the steps of fitting the pad of FIG. 8 upon a wearer.

FIGS. 12 and 13 are perspective views showing the further steps of fitting a sheath over the sealant pad of FIG. 8.

DETAILED DESCRIPTION

Referring to FIGS. 1 and 2, numeral 10 generally designates the sealant pad component of the male urinary drainage device embodying this invention. The pad is integrally formed of a suitable resilient material which is not only deformable but also compressible and at least somewhat elasticly recoverable. To obtain these properties, the sealant pad may be prepared from a composition composed principally of an elastomeric material such as synthetic or natural rubber. One such material is described in U.S. Pat. No. 2,570,182, being composed of a blend of nitro rubber and polyvinyl chloride. A material of this kind has been sold under the name "Ensolite", by Uniroyal, Inc. Its use in a sheet arrangement for a male urinary drainage device is described in U.S. Pat. No. 4,187,851. Another such material is composed principally of polyisobutylene. This material has been used in ostomy rings and blankets, and has been sold under the name "Crixiline" by Danal Laboratories, Inc., St. Louis, Missouri. Other suitable materials can be formulated from gelled mixtures of hydrocolloids such as karaya or carboxymethyl cellulose and polyhydroxy alcohols such as glycerin or propylene glycol, which preferably includes a few percent of fumed silica, as described in co-pending application Ser. No. 185,003, filed Sept. 8, 1980 for "Protective Sealing Composition in Molded Form for Surgical Drainage Openings", having a common assignee with the present application. Also, to further improve the desired properties of such compositions for use in the present invention, a minor proportion of polyacrylamide resin can be incorporated, and cross-linked by gamma irradiation. See U.S. Pat. Nos. 4,115,339 and 4,258,715.

It will be observed from FIGS. 1 and 2 that the sealant pad may assume a generally planar condition and has inner and outer surfaces 10a and 10b, respectively. Both of such surfaces should be provided with a tackiness capable of producing a sticking action against dry surfaces and preferably wet surfaces as well. Any suitable pressure-sensitive adhesive which is waterproof, non-toxic, and non-irritating may be used to coat the inner and outer surfaces of the liner pad. Reference may be had to the disclosures of the aforementioned prior art for typical adhesives believed to be suitable for the purposes disclosed herein. Alternatively, the pad in its entirety may be formulated from a material which gives such surfaces their pressure-sensitive adhesive properties. In either case, the opposite surfaces of the pad have tacky or pressure-sensitive adhesive properties which allow the inner surface to seal and cling to a patient's skin, and the outer surface to seal and cling to an elastic penile sheath, when the device is in use as hereinafter described. Although the adhesive seal must be secure enough to prevent leakage and sheath removal under conditions of normal use, the adhesive attachment must not be so aggressive that it will prevent the liner from being peeled away by the user whenever removal is considered necessary or desirable, all as well known in the art in connection with the formulation of conventional medical pressure-sensitive adhesives.

The sealant pad includes a central ring portion 11 and at least one, and preferably two or more, radially projecting strap portions 12. If desired, the inner surface of the annular head portion 11 may be generally concave, as shown clearly in FIG. 2, to facilitate application of the pad and to promote conformity to the wearer. A central opening 13 extends through the ring and a plurality of V-shaped slits or recesses may radiate outwardly into the ring from opening 13 to help insure an effective fit for users of different penis size. In the preferred embodiment illustrated in the drawings, a pair of diametrically disposed slits 14 are provided, such slits being longitudinally aligned with a pair of radial straps 12; such slit arrangement is desirable because it produces the advantages described without significantly weakening the structure as a whole.

The second major component of the male urinary drainage device is an elastic sheath 20 shown in unrolled and unstretched condition in FIG. 7. The sheath includes a thin resilient cylindrical body portion 21, a tapering neck portion 22, and a reduced drainage tube portion 23, all such portions being integrally formed of a highly stretchable elastic material such as natural or synthetic rubber. It will be observed that the wall thickness of the cylindrical portion 21 is substantially less than that of the other portions 22, 23, and that the tapered neck portion 22 at its smaller end includes a plurality of convolutions or annular enlargements 24. Two such convolutions of graduated size are depicted, their purpose being to permit greater stretchability, bending, and twisting of the neck portion when the device is in use, and to do so with less chance that kinking or obstruction of the lumen might occur. Also, since the interior of the neck portion is enlarged at such convolutions, the convolutions increase the fluid capacity of the neck portion, providing a momentary reservoir to accommodate surges of fluid when the device is in use.

FIGS. 3–5 illustrate a sequence of steps in fitting the device upon a wearer. Sealant pad 10 may be supplied to the user with protective release strips of the type generally depicted in FIG. 8 (and described hereinafter) extending over the inner and outer surfaces 10a and 10b. For clarity of illustration, and because such release strips might conceivably be omitted or at least not utilized in the manner hereinafter described, FIGS. 3 and 4 show sealant pad 10 being fitted in place without utilizing the release strips or sheets. As indicated in FIG. 3, the user draws the pad into place by turning the strap portions 12 rearwardly in generally the same direction and, with such strap portions being used as handles to draw the pad into position, the inner or rear surface 10a of the central ring portion 11 is urged into contact with the head or glans 30 of penis 31. To insure a proper fit, the deformable ring portion is stretched to a limited extent as it is pulled into engagement with glans 30 and, depending on the size of the organ, the opening 13 of the ring expands to a greater or lesser extent to insure conformity between the conically-deformed ring and head 30. The compressible or deformable material of the sealant pad is then molded against the penis to insure a conforming fit (FIG. 4).

Where release strips are provided, the procedure of fitting the pad into place is essentially the same except that the release strips are temporarily retained in place until the pad is ready to be adhered to the penis. Thus, as described hereinafter in connection with FIGS. 9 and 10, the pad may be drawn into place by strap portions 12, the inner or rear release strips may then be removed and the adhesive straps and ring portion brought into sealing contact with the penis, and thereafter, with the pad adhered in its final position, the outer or front release strips may then be removed from the pad.

Sheath 20 would normally be supplied with its cylindrical body portion 21 in rolled condition as indicated in FIG. 4 and by broken lines 21' in FIG. 7. The rolled sheath is simply drawn towards the pad-covered head portion of the penis until the inner surface of tapered portion 22 of the sheath sealingly engages the exposed outer surface of ring portion 11 of the sealant pad. The cylindrical body of the sheath is then completely unrolled, or substantially completely unrolled, to cover the shaft 32 of the penis 31 and the strap portions 12 of the sealant liner pad extending along that shaft (FIG. 5). The reduced drainage tube portion 23 of the sheath is connected to a drain tube leading to any suitable fluid collection pouch or other container 25.

It is believed apparent from the foregoing that the annular portion or ring portion 11 of the sealant liner pad, when fitted and formed into the generally frusto-conical configuration shown most clearly in FIGS. 4 and 6, develops two annular liquid-tight seals, one against the inside surface of the stretched neck portion 22 of the sheath, and the other against the proximal portion of glans 30. The location of such fluid-tight seals is designated by numeral 26 in FIG. 6.

The generally parallel strap portions extending proximally along opposite sides of the penile shaft 32 serve as sheath retainers to maintain the integrity of the fluid-tight seals formed in zone 26. The strap portions 12 are in adhesive contact with both the shaft of the penis and the body 21 of the sheath, and effectively resist forces that might otherwise tend to pull the frusto-conical ring portion away from glans 30 or to stretch and dislodge the larger end of the neck portion of the sheath from portion 11 of the sealant pad. The straps thus function as sheath retention means, whereas the ring portion of the sealant pad, although assisting in sheath retention, serves primarily in providing a barrier against fluid backup and leakage.

The embodiment of FIGS. 8-13 is similar to the structure already described, the main differences relating to the construction and operation of sealant pad 110. Like pad 10, sealant pad 110 has a central ring portion 111 and at least one, and preferably two or more, radially projecting strap portions 112. An opening 113 extends through the ring and is dimensioned so that when the deformable sealant pad is stretched the ring portion 111 may be slipped over the head or glans 30 of penis 31. Therefore, unlike the ring portion 11 of the previous embodiment which is designed to cover a major portion of glans 30, ring portion 111 when properly fitted is disposed about the shaft 32 of the penis immediately behind the corona 30a of the glans (FIGS. 10 and 11). The corona therefore coacts with the ring portion to help retain the sealant pad in proper position.

Although ring portion 111 may be provided with slits or recesses similar to those designated by numeral 14 in FIG. 1, it is believed preferable to omit such slits in the embodiment of FIGS. 8-13 because of the relatively large size of opening 113 and the manner in which ring 111 is fitted upon the wearer. The material from which the sealant pad 110 is formed is the same as already described; that is, the pad is integrally formed of a resilient material which is substantially waterproof and is not only deformable and elastic but also compressible. In addition, both of its surfaces have tacky or pressure-sensitive adhesive properties. In use, sealant pad 110 functions in the same manner as pad 10, with the parallel strap portions 112 being in adhesive contact with both the penile shaft 32 and the body 21 of sheath 20, and with ring portion 111 adhesively contacting both the neck portion 22 of the sheath and the end of the penis along and just behind the corona ridge. The straps 112 thus function primarily to retain the sheath and the ring portion of the sealant pad functions primarily to provide a barrier against fluid backup and leakage.

Release strips or sheets 140 and 141 extend over the inner (rear) and outer (front) surfaces of pad 111, as depicted in FIGS. 8-10. Such release strips not only protect the tackiness of the surfaces of the sealant pad prior to use, but also greatly facilitate handling and fitting of the device by a wearer. As shown most clearly in FIG. 8, release sheet 140 is divided into two sections 140a and 140b along the symmetrical midline 142 of the pad. Each section may therefore be peeled away from the pad even after the penis has been inserted through central opening 113. To assist a user in the removal of such release strips, each strip may be provided with tabs 143 projecting beyond the periphery of the pad's ring portion 111. In addition, the strips may also be extended beyond the ends of strap portions 112 to provide end tabs 144.

The strips or sheets 140 and 141 may be formed of plastic film such as, for example, polyethylene film, or from other materials such as paper which have been treated so that they do not securely adhere to the tacky surfaces of the sealant pad. Strips formed of such materials are flexible but not highly stretchable, with the result that the strips perform the additional function of helping the pliable sealant pad 111 to retain its shape prior to use. If such strips are formed of such substantially non-stretchable material then the strips should be provided with slits 145 radiating outwardly from opening 113 to permit enlargement of that opening as the product is fitted upon a wearer. On the other hand, if the strips are formed of a more stretchable film, such as one composed of polyurethane or other suitable elastomer, such slits may be omitted and the sealant pad may be provided with a smaller opening that may be easily stretched and pulled over the glans.

FIGS. 9-13 illustrate the sequence of steps for fitting the drainage device on a wearer. With the release strips on opposite sides of the pad still in place, the user draws the ring portion 111 of the sealant pad over the head 30 of the penis (FIGS. 9 and 10). Thereafter, the sections 140a and 140b of the rear release strip or sheet are peeled away (FIG. 10) and the tacky rear surface of the sealant pad is urged into contact with the penile shaft portion immediately behind glans 30. The front release sheet 141 may be left in place during such operation, since premature exposure of the tacky outer surface of the sealant pad might make it more difficult to mold the pad into the desired shape and might also reduce the adhering and sealing properties of the pad's outer surface. When the pliable pad has been formed into its final shape, or into an approximation of that shape, the sections 141a and 141b of the release sheet 141 are stripped from the pad's outer surface (FIG. 11). Sheath 20 is then fitted over penis 31 and sealant ring 110 in the manner previously described (FIGS. 12 and 13).

A presently preferred composition for use in preparing the sealant pads (10 or 110) comprises a mixture of hydrocolloid, polyhydroxy alcohol, fumed silica, and polyacrylamide. A general formula for this type of composition is set out below.

| General Formula | |
| --- | --- |
| Ingredients | Parts by Weight |
| Hydrocolloid | 15-25 |
| Polyhydroxy alcohol | 50-70 |
| Fumed silica | 1-3 |
| Polyacrylamide resin | 5-20 |

In the above formula, the hydrocolloid may be karaya gum or other natural hydrocolloid such as gelatin, pectin, etc., or a synthetic gum such as carboxymethyl cellulose or hydroxyethyl cellulose, or mixtures thereof. The polyhydroxy alcohol is preferably glycerin, or mixtures of glycerin and propylene glycol, but other polyhydroxy alcohols can be used. An example of suitable fumed silicas are the Cab-O-Sil products of Cabot Corporation, Boston, Massachusetts. The polyacrylamide resin may be a "Reten" resin of Hercules, Incorporated, as described in U.S. Pat. Nos. 4,115,339 and 4,258,271. The cited patents also describe gamma irradiation cross-linking of the polyacrylamide resins, which is a desirable procedure in preparing the material for the sealant pads of the present invention. An example of a presently preferred specific formulation is as follows:

| Specific Formula | |
| --- | --- |
| Ingredients | Weight % |
| Karaya powder | 15.00 |
| Sodium carboxymethyl cellulose | 5.00 |

| -continued Specific Formula | |
|---|---|
| Ingredients | Weight % |
| Polyacrylamide (non-ionic) | 10.00 |
| Polyvinyl alcohol | 5.00 |
| Fumed silica | 2.00 |
| Glycerin | 59.73 |
| Propylene glycol | 3.05 |
| Methyparaben | 0.09 |
| Propylparaben | 0.02 |
| Butylparaben | 0.11 |
| | 100.00% |

In compounding the foregoing ingredients, a mixture can first be prepared of the liquid ingredients (glycerin, propylene glycol, and the parabens). Fume silica is then dispersed in the liquid mixture, and thereafter the other powder ingredients are added (karaya, carboxymethyl cellulose, polyacrylamide, and polyvinyl alcohol). The completed mixture is then molded to form the pads, or formed into sheets for use in preparing the pads. Either in pad or sheet form, the material is preferably subjected to gamma irradiation, preferably from a Cobalt-60 radiation source. The amount of radiation employed should be sufficient to sterilize the material, and to achieve cross-linking of the polyacrylamide resin. For example, a radiation level of 2.5 megarads is satisfactory. To increase tackiness, the final product is then coated with a conventional medical-grade vinyl acrylic pressure sensitive adhesive.

While in the foregoing, embodiments of the invention have been disclosed in considerable detail for purposes of illustration, it will be understood by those skilled in the art that many of those details may be varied without departing from the spirit and scope of the invention.

We claim:

1. A sealant pad for a male urinary drainage device, comprising a pad formed of resilient, compressible, deformable, and water resistant material having a ring portion means dimensioned to fit about a wearer's penis at the head end portion thereof and at least one integral strap portion projecting from said ring portion means and dimensioned to extend proximally in a generally longitudinal direction from said head end portion along the penile shaft; said ring portion means and said strap portion means of the pad being thereof provided with tacky adhesive inner and outer surfaces, said inner surfaces of said ring portion means and said strap portion means being adapted to adhesively and sealingly engage the penis and said outer surfaces of said ring portion means and strap portion means being adapted to adhesively and sealingly engage an elastic sheath fitted thereover.

2. The sealant pad of claim 1 in combination with an elastic sheath; said sheath having a generally cylindrical body portion, a reduced drainage tube portion, and a tapered neck portion interposed therebetween; said sheath being dimensioned to be fitted over said pad means when the latter is worn by a user, with said cylindrical body portion in engagement with the adhesive outer surface of said strap portion means and with the larger end of said tapered neck portion in fluid-sealing engagement with the adhesive outer surface of said ring portion means.

3. The structure of claim 2 in which said neck portion of said sheath is provided with a plurality of enlarged annular convolutions to permit deformation of said neck portion without occlusion of the opening therethrough and to provide increased internal capacity to accommodate surges of fluid in use.

4. The structure of claim 3 in which said convolutions are graduated in size from the end of said neck portion adjacent said drainage tube portion towards the larger end of said neck portion.

5. The structure of claims 3 or 4 in which said neck and drainage tube portions have wall thicknesses substantially greater than that of said cylindrical body portion.

6. The structure of claims 1 or 2 in which said sealant pad is provided with a plurality of circumferentially-spaced strap portion means extending radially from said ring portion means, said ring portion means being generally planar in configuration prior to use.

7. The structure of claim 6 in which said sealant pad is provided with two of said strap means; said strap means extending from said ring portion from diametrically opposite sides thereof.

8. The structure of claim 6 in which said ring portion includes a central opening and at least one expansion slit extending radially outwardly from said opening.

9. The structure of claim 8 in which a plurality of said expansion slits are provided, said slits corresponding in number with said strap portion means, and each of said slits being generally longitudinally aligned with one of said strap portion means.

10. The structure of claim 9 in which each of said slits is generally V-shaped in configuration.

11. The sealant pad of claim 6 in which inner and outer release sheets are removably adhered to the respective inner and outer surfaces of said pad and are provided with openings in register with the opening in said ring portion means; said release sheets being provided with tabs projecting beyond the outer periphery of said pad to facilitate stripping of said sheets from said pad, said inner release sheet being separable along a dividing line extending from the outer periphery thereof to said opening in said inner release sheet.

12. The sealant pad of claim 11 in which said outer release sheet is also separable along a dividing line extending from the periphery thereof to said opening in said outer release sheet.

13. The sealant pad of claim 11 in which said release sheets are formed of flexible but substantially non-stretchable sheet material.

14. The sealant pad of claim 13 in which said release sheets are provided with slits radiating outwardly from the openings thereof to permit enlargement of said openings when said pad is fitted upon a wearer with said release sheets in place upon said pad.

15. The sealant pad of claim 11 in which said release sheets are formed of flexible and stretchable sheet material to permit enlargement of the openings therein when said pad is fitted upon a wearer with said release sheets in place upon said pad.

16. A sealant pad for a male urinary drainage device, comprising pad means formed of resilient, compressible, deformable, and water resistant material; said pad means being ring-shaped with an opening therethrough dimensioned to receive the end portion of a wearer's penis and being provided with tacky adhesive inner and outer surfaces, said inner surface being adapted to adhesively and sealingly engage the penis and said outer surface being adapted to adhesively and sealingly engage an elastic sheath fitted thereover; and inner and outer release sheets removably adhered to the respective inner and outer surfaces of said pad means; said sheets being provided with openings in register with the opening in said pad means and having tabs projecting beyond the outer periphery of said pad means to facilitate stripping of said sheets from said pad means.

17. The sealant pad of claim 16 in which said inner release sheet is separable along a dividing line extending from the periphery thereof to said opening in said inner release sheet.

18. The sealant pad of claim 17 in which said outer release sheet is also separable along a dividing line extending from the periphery thereof to said opening in said outer release sheet.

19. The sealant pad of claim 16 in which said release sheets are formed of flexible but substantially non-stretchable sheet material.

20. The sealant pad of claim 19 in which said release sheets are provided with slits radiating outwardly from the openings thereof to permit enlargement of said openings when said pad means is fitted upon a wearer with said release sheets in place upon said pad means.

21. The sealant pad of claim 16 in which said release sheets are formed of flexible and stretchable sheet material to permit enlargement of the openings therein when said pad means is fitted upon a wearer with said release sheets in place upon said pad means.

* * * * *